United States Patent
De Bruyne et al.

(10) Patent No.: US 11,602,618 B2
(45) Date of Patent: Mar. 14, 2023

(54) DEVICE FORMING AN INFUSION CATHETER FOR TREATING AT LEAST ONE PARTIAL OR TOTAL OBSTRUCTION IN A PASSAGE, SUCH AS A BODY PASSAGE

(71) Applicant: HEXACATH, Rueil Malmaison (FR)

(72) Inventors: Bernard De Bruyne, Kraainem (BE); Nico Pijls, Waalre (NL); Gilles Charles Franklin Ascher, Neuilly sur Seine (FR)

(73) Assignee: HEXACATH, Rueil Malmaison (FR)

( * ) Notice: Subject to any disclaimer, the term of this patent is extended or adjusted under 35 U.S.C. 154(b) by 1099 days.

(21) Appl. No.: 16/306,288

(22) PCT Filed: May 31, 2017

(86) PCT No.: PCT/FR2017/051368
§ 371 (c)(1),
(2) Date: Nov. 30, 2018

(87) PCT Pub. No.: WO2017/207931
PCT Pub. Date: Dec. 7, 2017

(65) Prior Publication Data
US 2019/0290889 A1    Sep. 26, 2019

(30) Foreign Application Priority Data
Jun. 1, 2016 (FR) ...................................... 1654974

(51) Int. Cl.
*A61M 25/10* (2013.01)
*A61B 5/01* (2006.01)
(Continued)

(52) U.S. Cl.
CPC ............. *A61M 25/104* (2013.01); *A61B 5/01* (2013.01); *A61B 5/6853* (2013.01);
(Continued)

(58) Field of Classification Search
None
See application file for complete search history.

(56) References Cited

U.S. PATENT DOCUMENTS

| 4,771,782 A | 9/1988 | Millar |
| 4,966,148 A | 10/1990 | Millar |

(Continued)

FOREIGN PATENT DOCUMENTS

| EP | 1930045 A1 | 6/2008 |
| EP | 2389968 | 3/2015 |

(Continued)

OTHER PUBLICATIONS

English translation of Office Action issued for Japanese Patent Application No. 2018-563176, dated Mar. 9, 2021, 12 pages.

(Continued)

*Primary Examiner* — Manuel A Mendez
(74) *Attorney, Agent, or Firm* — Hamre, Schumann, Mueller & Larson, P.C.

(57) ABSTRACT

The invention relates to an infusion catheter device.
This catheter device 10 has an elongate, substantially tubular shape defining a longitudinal axis, a distal end (D) and a proximal end (P), configured to be introduced into a conduit (50) having an inner wall (54) and an outer wall (56) and comprising at least one partial or total obstruction (60) or occlusion to be treated, said device comprising, at its distal end (D), one or more infusion orifices (16, 18, 20, 22) for an infusion liquid (LI), and, upstream from the one or more infusion orifices, at the proximal side (P) of the infusion catheter (10), at least one obturating element (70) for temporary obturating, configured to treat said obstruction (60) or occlusion and to perform the infusion of the infusion liquid (LI) downstream from the obturating element (70) and in the obturating position.

(Continued)

This device is suitable in particular for cardiac surgery and interventional cardiology.

33 Claims, 4 Drawing Sheets

(51) Int. Cl.
  *A61B 5/00* (2006.01)
  *A61B 17/12* (2006.01)
  *A61M 25/00* (2006.01)
  *A61B 17/22* (2006.01)
  *A61M 25/09* (2006.01)

(52) U.S. Cl.
  CPC .... *A61B 17/1204* (2013.01); *A61B 17/12109* (2013.01); *A61B 17/12136* (2013.01); *A61M 25/007* (2013.01); *A61B 2017/22067* (2013.01); *A61B 2017/22082* (2013.01); *A61B 2017/22084* (2013.01); *A61B 2505/05* (2013.01); *A61M 2025/09175* (2013.01); *A61M 2025/1052* (2013.01)

(56) References Cited

U.S. PATENT DOCUMENTS

| | | | |
|---|---|---|---|
| 5,037,392 A * | 8/1991 | Hillstead | A61F 2/958 606/191 |
| 5,328,471 A * | 7/1994 | Slepian | A61L 24/0031 604/101.03 |
| 5,415,636 A * | 5/1995 | Forman | A61M 25/104 604/101.03 |
| 5,874,419 A | 2/1999 | Herrmann et al. | |
| 6,585,689 B1 | 7/2003 | Macoviak et al. | |
| 6,620,188 B1 * | 9/2003 | Ginsburg | A61F 7/123 607/105 |
| 6,689,097 B2 | 2/2004 | Thramann et al. | |
| 7,084,117 B2 | 8/2006 | Culler et al. | |
| 8,177,704 B1 | 5/2012 | Mohl et al. | |
| 2003/0013986 A1 * | 1/2003 | Saadat | A61B 5/015 600/549 |
| 2003/0050599 A1 | 3/2003 | Thramann | |
| 2004/0167467 A1 | 8/2004 | Harrison et al. | |
| 2005/0113798 A1 | 5/2005 | Slater et al. | |
| 2005/0239743 A1 | 10/2005 | Zomer et al. | |
| 2006/0142783 A1 | 6/2006 | Lewis et al. | |
| 2009/0018498 A1 | 1/2009 | Chiu et al. | |
| 2010/0198186 A1 | 8/2010 | Ackermann | |
| 2014/0323887 A1 | 10/2014 | Anderson et al. | |
| 2017/0189654 A1 * | 7/2017 | Schwartz | A61B 17/22 |

FOREIGN PATENT DOCUMENTS

| | | |
|---|---|---|
| EP | 3009161 A1 | 4/2016 |
| JP | H06504451 | 5/1994 |
| JP | H09117510 | 5/1997 |
| JP | H09505503 | 6/1997 |
| JP | H10500606 | 1/1998 |
| JP | 2006513771 | 4/2006 |
| JP | 2015120088 | 7/2015 |
| WO | 9112830 | 9/1991 |
| WO | 9422885 A1 | 10/1994 |
| WO | 9528196 | 10/1995 |
| WO | 9619255 | 6/1996 |
| WO | 2009049823 A1 | 4/2009 |
| WO | 2012164481 A1 | 12/2012 |

OTHER PUBLICATIONS

International Search Report issued for International Patent Application No. PCT/FR2017/051368, 9 pages including English translation.

Van'T Veer, M. et al., "Continuous infusion thermodilution for assessment of coronary flow: Theoretical background and in vitro validation," Medical Engineering & Physics, 31, 2009, pp. 688-694.

Aarnoudse, W. et al., "Direct Volumetric Blood Flow Measurement in Coronary Arteries by Thermodilution," Journal of the American College of Cardiology, vol. 50, No. 24, 2007, pp. 2294-2304.

Camenzind, E. et al., "Site-Specific Intracoronary Delivery of Octreotide in Humans: A Pharmacokinetic Study to Determine Dose-Efficacy in Restenosis Prevention," Journal of Cardiovascular Pharmacology, vol. 43, Issue 1, Jan. 2004, pp. 133-139.

* cited by examiner

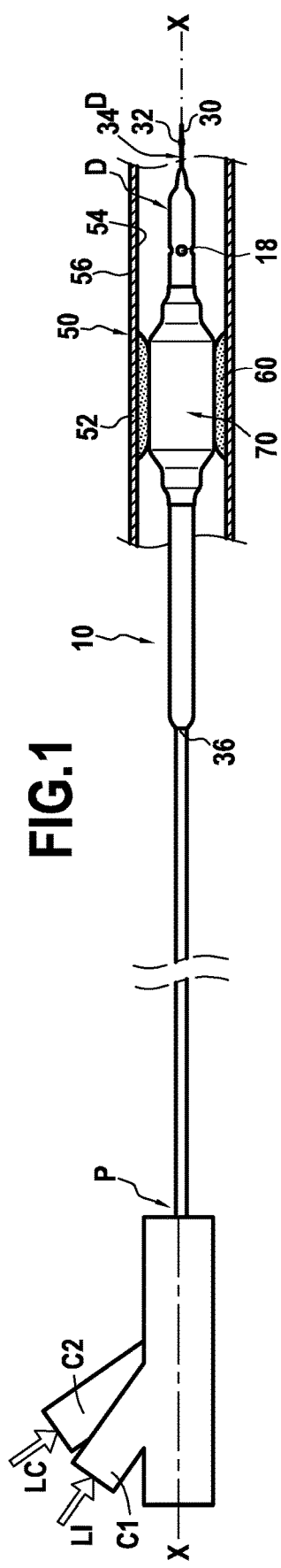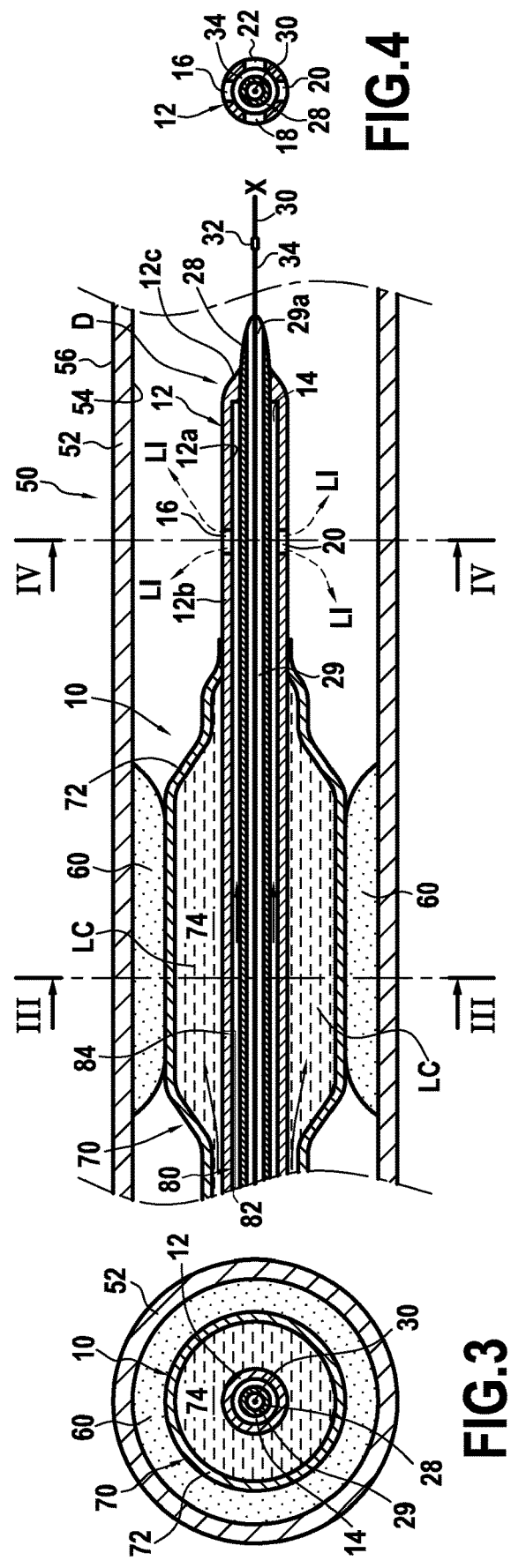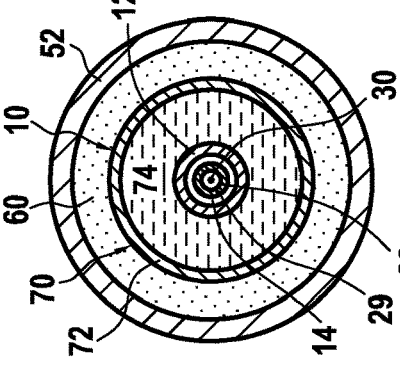

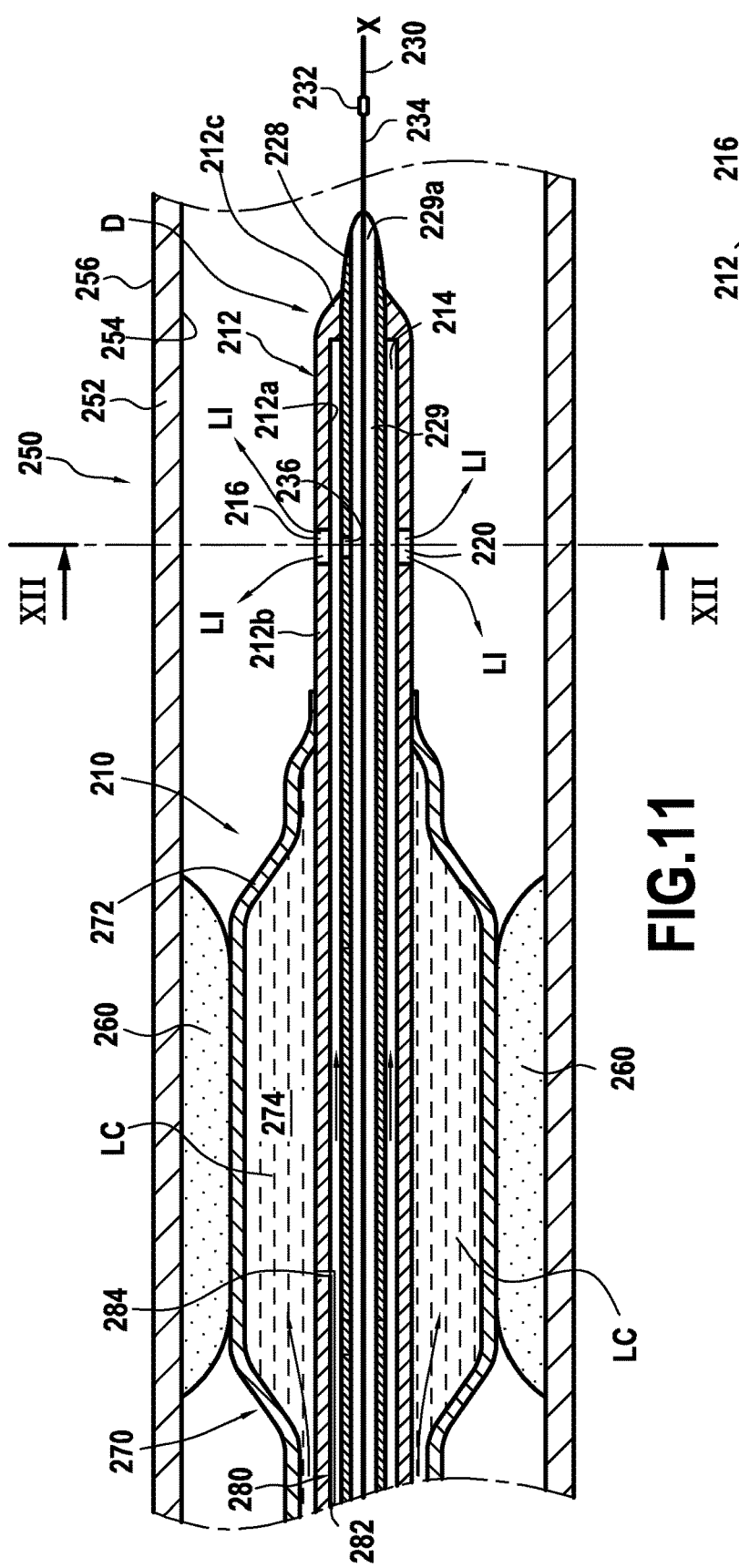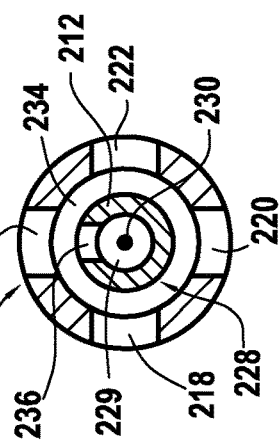

DEVICE FORMING AN INFUSION CATHETER FOR TREATING AT LEAST ONE PARTIAL OR TOTAL OBSTRUCTION IN A PASSAGE, SUCH AS A BODY PASSAGE

The invention relates to an infusion catheter device designed to be able to be introduced into a conduit comprising at least one partial or total obstruction to be treated. In particular, the invention relates to an infusion catheter device which can be introduced into a channel of the body of an animal or human being, chosen from the group consisting of a blood vessel, an artery, a coronary artery, the urinary tract, the esophagus and a pulmonary alveolus. The invention more particularly relates to a catheter device for cardiac surgery and interventional cardiology, particularly for treating a coronary artery occlusion resulting in a myocardial infarction, with improved survival of the part of the heart muscle that depends on this artery.

PRIOR ART

Firstly, the document U.S. Pat. No. 4,771,782 from Millar discloses a method and a device for introducing multiple catheters into a biological vessel. According to a first embodiment shown in FIGS. 1 to 7, this catheter device comprises a first conduit for the passage of a flexible guidewire 10, and a pressure sensor element 12, having various possible configurations, and, according to the embodiment of FIG. 2, also a second channel for introducing an infusion catheter 32 for infusing a contrast liquid that can be used for positioning the guidewire 10 and the catheter device or several catheter devices.

The pressure sensor can detect the blood pressure and can be used in cooperation with other sensors for detecting the temperature, pH, and even Doppler sensors. It is noted that this device can be useful in a variety of applications including the venous system, the urinary tract and the esophagus (see the abstract, figures and claims).

Similarly, the document U.S. Pat. No. 4,966,148 from Millar describes additional embodiments complementing those described in the preceding Millar document U.S. Pat. No. 4,771,782, hence this US patent is a continuation or CIP.

Also known from the article by Van't Veer et al., including Mr Pijls, published in Medical Engineering and Physics 31 (2009) 688-694, are a method and a device for thermodilution by continuous infusion for determining the coronary blood flow.

Under section 2.3 entitled "Measurement protocol" on pages 689 and 690, there are two infusion catheter embodiments comprising a central tube for passage of a guidewire for insertion into the blood vessel formed by a coronary artery, said catheter comprising, toward its distal end, a plurality of lateral orifices equidistant from each other at 3 cm from the end of the catheter, and an embodiment with four orifices arranged between 0.5 cm and 1 cm from the distal end of the catheter.

The article by Aarnoudse et al., including Mr Pijls and Mr De Bruyne, published in the Journal of American College of Cardiology, volume 50, no. 24, 2007, pages 2214-2304, discloses another embodiment of this thermodilution catheter introduced into the coronary artery and introduced near a stenosis in which the infusion catheter is advanced by sliding on a central guidewire provided at its distal end with a temperature sensor and introduced by a Y-shaped connector, conduit Y1 (see FIG. 1, page 2296), such that the temperature sensor is arranged further downstream from the distal end of the catheter, whilst the catheter has its distal end arranged in proximity to the stenosis. In the embodiment described, an inflatable perivascular occlusion device is provided downstream from the distal end of the catheter. A second Y-shaped connector is used to inject a saline solution at room temperature and at a rate of 8 to 25 ml/min into the infusion channel of the catheter. The coronary pressure measurement and the temperature are recovered on a Radi analyzer interface and displayed. The pressure is measured at the distal end of the guide catheter and is recorded by regular pressure transducer and displayed on the interface. The tests carried out in humans were identical to those in dogs, except that the perivascular flow sensor and the occlusion device were different. The catheter used had a distal end tapered or inclined so as to limit the flow rate of the closest orifice of the four orifices provided in the last 5 mm from the distal end of the infusion catheter.

Moreover, the document US 2005/113798 from Slater discloses a method and a device for treating the interior of a blood vessel, which may have various embodiments, including the number and arrangements of the lateral infusion orifices for the infusion fluid, generally composed of a saline solution. There may be provided an inflatable balloon at the distal end of the infusion catheter, further downstream from the infusion orifices arranged upstream, at the proximal side before said balloon (see, for example, FIGS. 29 to 32 of this document).

Moreover, the document WO 2009/049823 from Regittnig describes a catheter comprising a first tubular element defining a first lumen and a first perforation, and a second tubular element defining a second lumen and a second perforation, in which the second tubular element is configured to receive the first tubular element so as to define a chamber between the two, and having one end of the second tubular element in contact with the end of the first tubular element. The first and second tubular elements are arranged so as to provide a first fluid passage through the first perforation to an observation body and a second fluid passage through the second perforation from the observation body and into the chamber (see FIGS. 1 to 10).

The document US 2014/0323887 from Anderson, Boston Scientific, moreover describes a thermodilution catheter system and a method for determining the blood flow rates. According to this document, the catheter comprises a fluid channel 82 defined between an inner tubular element 14 and an outer tubular element 12 for providing an indicator fluid, and a channel for the guidewire 30 defined by the inner tubular element, one of the infusion fluid openings 40 being formed at the distal end of the outer tubular element allowing the fluid to pass to the outside of the catheter and the inside of the blood conduit 80. In order to detect the temperature of the fluid at its exit to the outside, the guidewire 30 comprises a temperature sensor 32 positioned opposite an orifice 50 provided in the distal wall of the inner tubular element 14 in order to receive a flow of the fluid and to measure its temperature (see the figures and abstract). For diffusion to the outside of the outer tube of the infusion catheter, several orifices can be provided at an equal distance on the same axial plane of the catheter (see FIG. 1A).

Furthermore, the document WO 2012/164481 from Hooft et al. describes a system for measuring blood flow using an optical approach, particularly an optical fiber.

Moreover, the document EP 1 930 045 from Czygan et al. discloses an implantable medical device having acoustic sensors for measuring the mitral blood flow.

The patent U.S. Pat. No. 6,585,689 B1 (inventor Macoviak) also discloses an aortic catheter having an upstream occlusion element positioned in the ascending aorta and a downstream anchoring element positioned in the descending aorta downstream from the aortic arch (see the flyleaf of the patent, and FIG. 27 corresponding thereto).

The purpose of this aortic catheter is to induce cardioplegic arrest in order to selectively segment and perfuse the aorta during the cardiopulmonary bypass.

The aim of the invention described below is completely different from that of said patent, which is also specific to the aortic arch, unlike the catheter of the invention which allows multiple uses.

The patent U.S. Pat. No. 6,689,097 B2 (inventor Thramann) moreover discloses a catheter with what is called a "flow-by" channel, which includes a catheter deployed "over the wire", which is positioned just below the occluded artery, according to a standard procedure. The flow-by channel then shunts the blood and thus renders all of the atherostenotic plaque friable, from the high-pressure carotid occlusion as far as the negative pressure end in order to effectively reverse the flow of blood through the obstructed or occluded artery. The stent is then advanced into the artery and deployed. According to Thramann, the vascular catheter affords the advantage of a collateral blood flow to solve the problem of stroke during endovascular procedures (see the abstract).

It is thus noted that the structure described is completely different and seeks to solve the problem of occlusion or atherosclerosis in an entirely different way from the invention described below.

The document U.S. Pat. No. 5,415,636 from Forman discloses a catheter device provided with a dilation balloon 24, and also an inner catheter that comprises orifices 56 for delivery of medicament(s).

However, the medicament delivery orifices are in a retracted position relative to the balloon when the latter is in the dilated state, and the outer catheter comprising the balloon has to be retracted in order to uncover the medicament delivery orifices for injection of the medicament.

Therefore, the structure of the device is different from the structure of the device according to the invention described below.

The document U.S. Pat. No. 8,177,704 from Mohl discloses a catheter having an inflatable balloon 122 and also orifices 129 downstream from the balloon 122.

However, these downstream orifices 129 are not used for injecting a liquid but instead for detecting characteristics of the blood located downstream from the inflatable balloon, such as the blood pressure and the blood temperature by the presence of sensor devices which are located inside a central lumen 125 (see FIGS. 4 and 5).

This document from Mohl is absolutely not relevant as regards the invention described below.

The document EP 3 009 161 from Innovation for Heart and Vessels provides an intravascular microcatheter which serves to deliver active substances such as medicaments and which, according to the first embodiment, comprises pores 5 that are distributed uniformly in a high number of 20 to 200 at the downstream end or distal end of the catheter 3.

In a second embodiment, there is an inflatable balloon 9 (see FIGS. 4 and 5).

It is specified that the balloon is designed to provide a proximal occlusion of the vessel (paragraph [0012], column 3, lines 29-31), so as to improve the efficiency of the delivery of the active substances to the target location only, by preventing the return of the active substances, which is especially beneficial in the case of the use of toxic drugs such as cytostatics, and the balloon also stabilizes the catheters (see column 3, lines 31-35).

However, here the balloon is not intended to have the function of treating an obstruction, and this represents a fundamental difference in relation to the invention described below.

The document US 2010/198186 also provides a catheter having an inflatable balloon and the possibility of injecting a fluid agent through the lumen, which serves the guide wire, this fluid agent being in practice a contrast liquid. The fluid flow orifices 310b are provided downstream from the balloon (see in particular FIG. 5 and FIG. 1, and also the passage at column 4, lines 1 to 9, prior to paragraph [0041]; see also paragraph [0049] on the embodiment of FIG. 5).

Contrary to the invention described below, there is no function of treating an obstruction using the inflatable balloon.

Another non-relevant document is US 2009/018,498 from Chiu.

TECHNICAL PROBLEMS TO BE SOLVED BY THE INVENTION

A main aim of the present invention is to solve the new technical problem which entails affording a solution that permits treatment of at least one partial or total obstruction or occlusion in a conduit while at the same time being able to carry out a treatment of the wall of the conduit in which the obstruction or occlusion is located, and at least downstream from there.

A main aim of the present invention is also to solve this new technical problem by affording a solution which permits treatment of any type of partial or total obstruction in a conduit, in particular in a conduit formed by a channel of the body of an animal or human being, chosen from the group consisting of a blood vessel, an artery, a coronary artery, the urinary tract, the esophagus and a pulmonary alveolus, while at the same time being able to treat the wall of the conduit in which the obstruction or occlusion is located, and at least downstream from there.

A main aim of the invention is also to solve the new technical problem by affording a solution in the form of a catheter device for cardiac surgery, especially to treat a coronary artery occlusion resulting in a myocardial infarction, with improved survival of the part of the heart muscle that depends on this artery.

A main aim of the present invention is also to solve the new technical problem which entails affording a solution that permits treatment of a partial or total obstruction or occlusion of a blood conduit, with hypothermic treatment downstream from said partial or total obstruction or occlusion and while the obstruction or occlusion is treated simultaneously, so as to prevent any further degradation of the tissues downstream from the obstruction or occlusion.

It is also an aim of the invention to solve these technical problems by affording a solution that is of simple construction, permitting easy and reliable manufacture, reproducible industrially and medically.

SUMMARY OF THE INVENTION

Thus, according to a first aspect, the invention relates to an infusion catheter device having a distal end and a proximal end, configured to be introduced into a conduit having an inner wall and an outer wall and comprising at least one partial or total obstruction or occlusion to be treated, said device comprising at its distal end, on said outer wall, one or more infusion orifices for an infusion liquid, and, upstream from the one or more infusion orifices, at the proximal side of the infusion catheter, on said outer wall, at least one obturating element for temporary obturating, configured to treat said obstruction or occlusion, movable between a non-obturating rest position and a obturating working position, and to perform the infusion of the infusion liquid downstream from the obturating element in the obturating position thereof.

According to a second aspect, the invention relates to an infusion catheter device having a distal end and a proximal end, configured to be introduced into a conduit having an inner wall and an outer wall and comprising at least one partial or total obstruction or occlusion to be treated, said device comprising at its distal end, on said outer wall, one or more infusion orifices for an infusion liquid, and, upstream from the one or more infusion orifices, at the proximal side of the infusion catheter, on said outer wall, at least one obturating element for temporary obturating, configured to treat said obstruction or occlusion, movable between a non-obturating rest position and a obturating working position, to perform the treatment of at least one partial or total obstruction or occlusion present in a conduit which is advantageously a channel of the body of an animal or human being, chosen from the group consisting of a blood vessel, an artery, a coronary artery, the urinary tract, the esophagus and a pulmonary alveolus, and to simultaneously perform the infusion of the infusion liquid downstream from the sealing element in the sealing position thereof.

According to a third aspect, the invention also makes available a method for treating a partial or total obstruction to be treated in a conduit having an inner wall and an outer wall, said conduit being formed by a channel of the body of an animal or human being, chosen from the group consisting of a blood vessel, an artery, a coronary artery, the urinary tract, the esophagus and a pulmonary alveolus, said method comprising the provision of a catheter device configured to be able to be introduced into said conduit comprising at least one partial or total obstruction or occlusion to be treated, said device comprising, at its distal end, one or more infusion orifices for an infusion liquid, and, upstream from the one or more infusion orifices, at the proximal side of the infusion catheter, at least one obturating element for temporary obturating, configured to treat said obstruction or occlusion, movable between a non-obturating rest position and a obturating working position, comprising:

the introduction of said catheter device into said conduit, this introduction being performed while the obturating device is in the rest position, until the obturating device is arranged near, particularly inside, the partial or total obstruction or occlusion;

the guidewire is introduced through the catheter until its distal end is arranged downstream from the partial or total obstruction in said conduit; or vice versa;

the placement of the obturating element in the temporary obturating position in order either to define a confined space arranged between the outer wall of the catheter device and the inner wall of the conduit to be treated, and the partial or total obstruction of said conduit, or to treat the obstruction or occlusion by compression;

the infusion of the infusion liquid, either in said confined space, or downstream from the obstruction or occlusion, through said infusion orifices, in order to ensure either the treatment of said partial or total obstruction present in said channel or the treatment of the conduit walls downstream from said obstruction or occlusion.

According to a particular embodiment, the infusion liquid is a liquid brought to a temperature protecting the material or tissues of the wall of the conduit. This temperature can be a temperature that is sufficiently cold to hibernate the tissues of the channel to be protected during a predetermined period of time. A person skilled in the art knows how to determine the temperature for protection of the surrounding tissues downstream from the obstruction or occlusion.

Thus, in cardiac surgery, during the occlusion maintained by the obturating element in the working position of occlusion, it is possible, for example, to infuse an infusion liquid brought to a temperature 6 to 8° C. below the blood temperature for a period of 5 to 15 minutes, in particular about 10 minutes. The temperature is measured by virtue of the presence of a temperature sensor situated downstream from the infusion orifices, either on the catheter or on the guidewire. Under these conditions, the temperature of the surrounding tissue is about 3 to 6° C., in particular about 4° C., below that of the blood.

By virtue of the invention, it is possible to treat a partial or total obstruction to be treated in any channel, in particular in a channel of the body of an animal or human being, chosen from the group consisting of a blood vessel, an artery, a coronary artery, the urinary tract, the esophagus, a pulmonary alveolus, without limitation, while simultaneously treating the wall of the channel downstream in order to protect the material or the tissues forming said wall.

In the case of the channel of the body of an animal in the context of a blood vessel, an artery or a coronary artery, this is generally a thrombosis, a stenosis or a clot. In the urinary tract, it is generally a concretion or calculus, for example a calculus of the bladder or of the kidneys or urethra.

DETAILED DESCRIPTION OF THE INVENTION

According to a first aspect, the invention relates to an infusion catheter device having an elongate, substantially tubular shape defining a longitudinal axis, an outer surface and an inner surface and defining a distal end (D) and a proximal end (P), configured to be introduced into a conduit having an inner wall and an outer wall and comprising at least one partial or total obstruction or occlusion to be treated, said device comprising, at its distal end (D), on said outer wall, one or more infusion orifices for an infusion liquid (LI), and, upstream from the one or more infusion orifices, at the proximal side (P) of the infusion catheter, on said outer wall, at least one obturating element for temporary obturating, movable between a non-obturating rest position and a obturating working position, configured to treat said obstruction or occlusion and to perform the infusion of the infusion liquid (LI) downstream from the obturating element and in the obturating position.

According to a particular embodiment, the device according to the invention is characterized in that said device comprises:

a. a first substantially tubular element, made of a flexible but substantially non-expandable and substantially non-collapsible material, configured to define a first channel for receiving a guidewire, and having an outlet opening at the distal end (D) of the device;

b. a second substantially tubular element made of a flexible but substantially non-expandable and substantially non-collapsible material, configured to define a second channel for receiving the infusion liquid LI, said one or more infusion orifices passing through the wall of the second element of the device in order to infuse the infusion liquid LI from the second channel to the outside of the device.

It will be appreciated that, in the context of the invention, the diameter of the first channel and of the second channel is substantially constant at least at the region of the obturating element and in particular along the length of the catheter inside the conduit to be treated; and the diameter of each channel is independent of the rest position or occlusion position of the obturating element.

The diameter of the first channel can be different from the diameter of the second channel.

The materials for making the different elements of the catheter and the method of manufacture are well known to a person skilled in the art, especially from the prior art documents analyzed above. See, for example, Forman U.S. Pat. No. 5,415,636, column 4, line 50 to col 6, line 55; or US 2010/0198.186, § [0061], and also US 2009/018.498 from Chiu, § [0124] and [0131].

According to one variant, the second channel is closed in a leaktight manner at the distal end in order to force the infusion liquid to pass through the infusion orifices.

According to an embodiment variant, the first element is arranged coaxially with respect to the catheter device. In this case, according to one variant, the second element can also be coaxial, while having a larger diameter than the first element, thus being concentric and having its wall which constitutes the outer wall of the catheter device.

According to another embodiment variant, the first element is arranged with its axis parallel to the longitudinal axis of the catheter device, in particular so as to have a common wall with the second element of the catheter device, whilst, according to one variant, the second element can constitute the outer wall of the catheter device, thereby defining the second channel between the second element and the first element.

According to another particular embodiment, the device according to the invention is characterized in that the temporary obturating element comprises an inflatable balloon arranged outside the catheter device and supplied with inflation fluid through an inflation channel arranged inside or at the surface of the catheter, and in particular the balloon inflation fluid can comprise a diluted or undiluted contrast agent.

According to a particular characteristic, in order to ensure the passage of the infusion liquid with the balloon inflated, a pressure differential is employed: The super-compliant balloon deploys from 5/6 bar for a maximum pressure of about 14/15 bar, while the second channel, or infusion conduit, supports up to about 35/40 bar. It therefore suffices to increase the pressure of the infusion liquid in order to provide the desired infusion rate. In practice, the catheter is connected to an automatic injection pump for programming the rate.

According to another particular embodiment, the device according to the invention is characterized in that at least some infusion orifices are arranged on said outer wall at a distance from each other on the same axial plane of said catheter device.

According to a further particular embodiment, the device according to the invention is characterized in that at least some infusion orifices are arranged on said outer wall at a distance from each other on the same axis of said catheter device substantially parallel to the longitudinal axis of the device.

According to yet another particular embodiment, the device according to the invention is characterized in that the guidewire comprises at least one or more temperature sensors, of which at least one sensor is positioned on a distal part (D) of the guidewire in order to measure the temperature of the infusion fluid, downstream from the aforementioned infusion orifices, at the distal side of the catheter device.

According to another particular embodiment, the device according to the invention is characterized in that it comprises at least one or more temperature sensors, of which at least one sensor is positioned inside the catheter and close to at least one infusion orifice, in order to measure the temperature of the infusion fluid in situ before it leaves through the aforementioned infusion orifices, at the distal side of the catheter device.

According to another particular embodiment, the device according to the invention is characterized in that it comprises at least one inner orifice communicating with the chamber defined between the inner tubular element and the outer tubular element and in which circulates the infusion liquid LI, at at least one of the outer orifices for infusion of the infusion liquid LI to the outside of the catheter, in order to measure the temperature of the infusion liquid, by virtue of the presence of the guidewire provided with a temperature sensor element movable downstream from the outside until it lies opposite the inner orifice.

According to another particular embodiment, the device according to the invention is characterized in that it comprises a proximal channel C1 for infusion of the infusion liquid LI, which can be a heat-transfer liquid introduced at a temperature below the temperature prevailing inside said conduit.

According to a further particular embodiment, the device according to the invention is characterized in that, when the obstruction or occlusion can be dissolved in a suitable liquid, for example a kidney stone or gallstone, it comprises a proximal channel C1 for infusion of the infusion liquid, which can be an infusion liquid comprising a product that dissolves the obstruction or occlusion. A person skilled in the art will know the dissolving products that can be used. A product dissolving a calculus is, for example, ammonium chloride NH4Cl or ammonium nitrate NH4NO3.

According to another particular embodiment, the device according to the invention is characterized in that it comprises a proximal channel C1 for infusion of the infusion liquid, which can be a liquid comprising at least one medicament for treating the tissues near the obstruction or occlusion. A person skilled in the art will know the medicaments that can be used. As a medicament, it is possible to use an aqueous suspension or dispersion of a medicament for inhibiting restenosis, for example a polyionic cyclodextrin derivative combined with a growth factor, in particular a growth factor that binds heparin, as described in the document U.S. Pat. No. 5,874,419; or another restenosis-inhibiting medicament comprising a saline solution containing octreotide, in particular radiolabeled with 111In (indium 111), for example at a dose of 0.02 µg per infused ml infused concomitantly with heparin, at a rate of 200 IU/ml, as described in the article by Camezind et al. in Journal of Cardiovascular Pharmacology, volume 43, no. 1, January 2004 or US 2005/0239743; a medicament for performing antithrombotic treatment or a medicament that promotes wound healing, in an effective amount for inducing a response in the form of healing/recovery of the damaged tissues adjacent to and downstream from the obstruction or occlusion, for example comprising or consisting of a non-reducing saccharide or a sulfated analog thereof such as a non-reducing monosaccharide or disaccharide or a sulfated analog thereof, for example glucose, sucrose, fructose, or a sulfated analog thereof, in particular a sodium sucrose octasulfate solution, described in the document WO 94/22885; a somatostatin receptor 1 agonist, as described in the document U.S. Pat. No. 7,084,117; a prodrug of NO, for example chosen from L-arginine, L-lysine, or mixtures thereof; another anti-restenosis agent can be chosen from a medicament for inhibiting smooth muscle cell proliferation, an inhibitor of the cytoskeleton, and a macrocyclic triene antibiotic. This anti-restenosis agent may be water soluble or water insoluble. As examples of a water-soluble anti-restenosis agent, the latter may belong to the family of peptides, whilst an example of a water-insoluble medicament is a medicament belonging to the limus family.

According to a further particular embodiment, the device according to the invention is characterized in that the guidewire comprises at least one or more temperature sensors, of which at least one sensor is positioned on a distal part of the guide in order to measure the temperature of the infusion fluid infused after the aforementioned infusion orifices, at the distal side of the catheter device, downstream or upstream from the obstruction or occlusion in said conduit.

According to a further particular embodiment, the device according to the invention is characterized in that it comprises at least one or more temperature sensors, of which at least one temperature sensor is positioned inside the catheter and close to at least one infusion orifice, in order to measure the temperature of the infusion liquid in situ before it leaves through the aforementioned infusion orifices, at the distal side of the catheter device.

According to a further particular embodiment, the device according to the invention is characterized in that it comprises at least one inner orifice communicating with the chamber defined between the inner tubular element and the outer tubular element and in which circulates the infusion liquid, at the outer orifices for infusion of the infusion liquid to the outside of the catheter, in order to measure the temperature of the infusion liquid, by virtue of the presence of the guidewire provided with a temperature sensor element movable downstream from the outside until it lies opposite the inner orifice.

According to another particular embodiment, the device according to the invention is characterized in that it comprises at least one visual marking system at a proximal position and/or at an intermediate position of the catheter device, and/or at a distal position, allowing the medical personnel to precisely locate the catheter device inside the conduit to be treated.

According to a further particular embodiment, the device according to the invention is characterized in that the visual marking system comprises one or more radiopaque markers.

According to another particular embodiment, the device according to the invention is configured to be introduced into the aforementioned conduit, which is a channel of the body of an animal or human being, chosen from the group consisting of a blood vessel, an artery, a coronary artery, the urinary tract, the esophagus and a pulmonary alveolus.

According to a second aspect of the invention, the invention relates to an infusion catheter device having a distal end and a proximal end, configured to be introduced into a conduit having an inner wall and an outer wall and comprising at least one partial or total obstruction or occlusion to be treated, said device comprising at its distal end, on said outer wall, one or more infusion orifices for an infusion liquid, and, upstream from the one or more infusion orifices, at the proximal side of the infusion catheter, on said outer wall, at least one obturating element for temporary obturating, configured to treat said obstruction or occlusion, movable between a non-obturating rest position and a obturating working position, in order to perform the treatment of at least one partial or total obstruction or occlusion present in a conduit which is advantageously a channel of the body of an animal or human being, chosen from the group consisting of a blood vessel, an artery, a coronary artery, the urinary tract, the esophagus and a pulmonary alveolus, and to simultaneously perform the infusion of the infusion liquid downstream from the obturating element in the obturating position thereof.

According to a third aspect, the invention also relates to a method for treating at least one partial or total obstruction or occlusion present in a conduit, said method comprising:
  the introduction of a catheter device into said conduit, said catheter device being as defined according to any embodiment defined for the first aspect described above or below, in particular equipped with a temperature sensor at its distal end; this introduction being performed while the obturating device is in the rest position, until the obturating device is arranged near, particularly inside, the partial or total obstruction or occlusion;
  the guidewire is introduced through the catheter until its distal end is arranged downstream from the partial or total obstruction in said conduit;
  the placement of the obturating element in the temporary obturating position in order either to define a confined space arranged between the outer wall of the catheter device and the inner wall of the conduit to be treated, and the partial or total obstruction of said conduit, or to treat the obstruction or occlusion by compression;
  the infusion of the infusion liquid, either in said confined space or downstream from the obstruction or occlusion, through said infusion orifices, in order to ensure either the treatment of said partial or total obstruction present in said channel or the treatment of the conduit walls downstream from said obstruction or occlusion.

In a particular embodiment, this method entails the use of a heat-transfer infusion liquid regulated to a temperature for thermal treatment of the walls of the conduit downstream from the obstruction or occlusion.

In particular, when the aforementioned conduit is a channel of the body of an animal or human being, chosen from the group consisting of a blood vessel, an artery, a coronary artery, the urinary tract, the esophagus and a pulmonary alveolus, the temperature of the infusion liquid is regulated in order to obtain hypothermia of the tissues of said channel of the body.

According to a particular embodiment, following this thermal treatment, the method of the invention comprises a surgical treatment by inserting an expansion device such as a stent, well known to a person skilled in the art, into the region of the obstruction or occlusion.

According to a particular embodiment variant, this method also entails, after this expansion, a post-operative thermal treatment using the catheter device according to the invention in the region of the partial or total obstruction in said conduit, in order to improve the recovery of the tissues of the body channel.

Thus, in cardiac surgery, during the occlusion maintained by the obturating element in the working position of occlusion, it is possible, for example, to infuse an infusion liquid brought to a temperature 6 to 8° C. below the blood temperature for a period of 5 to 15 minutes, in particular about 10 minutes. The temperature is measured by virtue of the presence of a temperature sensor situated downstream from the infusion orifices, either on the catheter or on the guidewire. Under these conditions, the temperature of the surrounding tissue is about 3 to 6° C., in particular about 4° C., below that of the blood.

By virtue of the invention, it is possible to treat a partial or total obstruction to be treated in any channel, in particular in a channel of the body of an animal or human being, chosen from the group consisting of a blood vessel, an artery, a coronary artery, the urinary tract, the esophagus, a pulmonary alveolus, without limitation, while simultaneously treating the wall of the channel downstream in order to protect the material or the tissues forming said wall.

In the case of the channel of the body of an animal in the context of a blood vessel, an artery or a coronary artery, this is generally a thrombosis, a stenosis or a clot. In the urinary tract, it is generally a concretion or calculus, for example.

According to the invention, all of the particular embodiments of the first aspect naturally apply to the second aspect and to the third aspect.

A person skilled in the art will readily appreciate that the invention makes use of a simple device which is easy to manufacture, safe and reliable at an industrial scale and medically, and with which it is possible to treat different types of obstructions or occlusions in different types of channels.

DESCRIPTION OF THE DRAWINGS

FIG. 1 shows a schematic view of a first embodiment of a catheter device according to the present invention provided with a obturating element such as an inflation balloon upstream from the infusion orifices in the working position in a channel, such as a coronary artery, shown in an enlarged partial longitudinal axial section.

FIG. 2 shows a longitudinal axial sectional view of the device from FIG. 1, at the obstruction or occlusion, showing the obturating element in the working position, here compressing the obstruction or occlusion, and showing the infusion of the infusion liquid downstream from the obstruction.

FIG. 3 shows an axial cross-sectional view along the section line III-III of FIG. 2.

FIG. 4 shows an axial cross-sectional view along the section line IV-IV of FIG. 2.

FIG. 11 shows an axial sectional view, similar to FIG. 2, of a third embodiment of a catheter device according to the present invention provided with a obturating element such as an inflation balloon positioned at and inside the obstruction to be treated.

FIG. 12 shows an axial cross-sectional view along the section line XII-XII of FIG. 11.

EXAMPLE 1 OF CATHETER ACCORDING TO THE INVENTION

Figure 5:
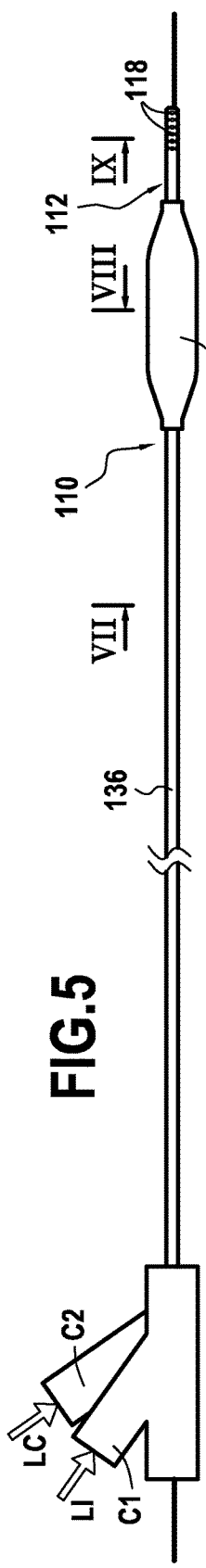
FIG. 5 shows a schematic view of a second embodiment of a catheter device according to the present invention provided with a obturating element such as an inflation balloon.
Figure 6:
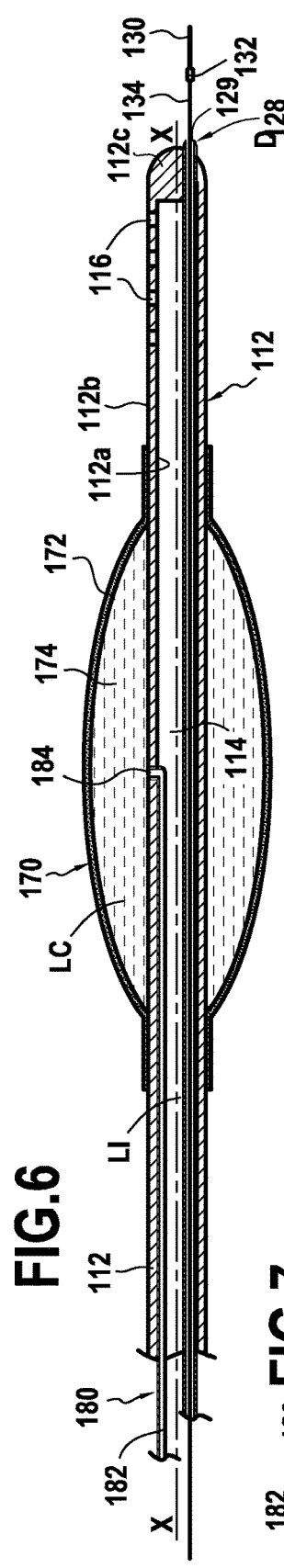
FIG. 6 shows an axial sectional view of the second catheter device according to the invention from FIG. 5, with its obturating element in said working or inflated position in order to better see the device.
Figure 7:
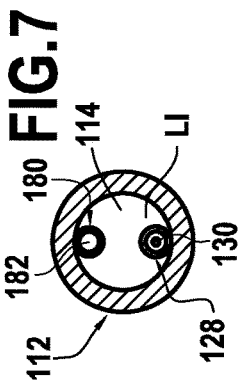
FIG. 7 shows an axial cross-sectional view along the section line VII-VII of FIG. 5.
Figure 8:
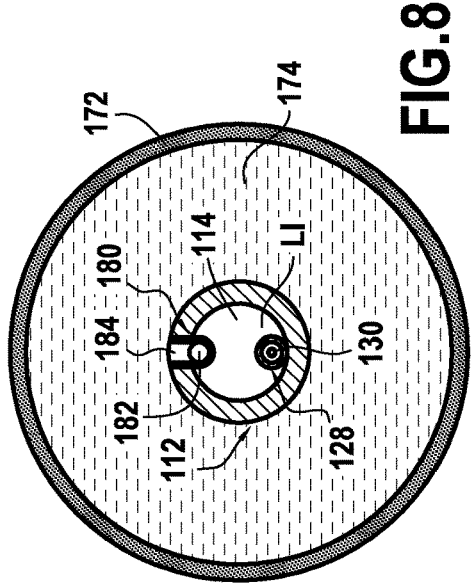
FIG. 8 shows an axial cross-sectional view along the section line VIII-VIII of FIG. 5.

Referring to FIGS. 1 to 4, a first embodiment of a catheter device is shown having the general reference number 10, configured to be introduced into a conduit having an inner wall and an outer wall and comprising at least one partial or total obstruction or occlusion to be treated, said device 10 has an elongate, substantially tubular shape defining a proximal end P and a distal end D, a longitudinal axis X-X, and having a substantially tubular outer wall 12 defining an outer surface 13 and an inner surface 14.

According to the invention, said device 10 also has at its distal end (D), on said outer wall 12, one or more infusion orifices 16, 18, 20, 22 for an infusion liquid (LI), and, upstream from the one or more infusion orifices, at the proximal side (P) of the infusion catheter, on said outer wall 12, at least one obturating element 70 for temporary obturating, configured to treat said obstruction or occlusion and to simultaneously perform the infusion of the infusion liquid (LI) downstream from the obturating element, and in the obturating position thereof.

According to a particular embodiment, the device according to the invention is characterized in that said device comprises:

a. a first substantially tubular element 28, which is made of a flexible but substantially non-expandable and substantially non-collapsible material, configured to define a first channel 29 for receiving a guidewire 30, and having an outlet opening 29a at the distal end (D) of the device;

b. a second substantially tubular element which is made of a flexible but substantially non-expandable and substantially non-collapsible material, configured to define a second channel 14 for receiving the infusion liquid LI; said one or more infusion orifices 16, 18, 20, 22 passing through the wall of the second element (12) of the device in order to infuse the LI infusion liquid from the second channel to the outside the device.

According to an embodiment variant, shown here in FIGS. 1 to 4, the second channel is closed at its distal end by a leaktight partition 12c in order to force the infusion liquid LI to pass through the infusion orifices 16, 18, 20 22.

According to another embodiment variant, the first element 28 is arranged coaxially with respect to the catheter device 10. In this case, according to one variant, as shown in FIGS. 1 to 4, the second element 12 can also be coaxial while having a larger diameter than the first element 28, thus being concentric and with its wall which constitutes the outer wall of the catheter device.

According to another particular embodiment, the device according to the invention is characterized in that the temporary obturating element 70 comprises an inflatable balloon 72 arranged outside the catheter device and supplied with inflation fluid through an inflation channel 80 arranged inside or at the surface of the catheter 10, having a lumen 82 opening into the interior 74 of the balloon 72 via an opening 84. In particular, the balloon inflation fluid, for example a gas such as air, or a liquid, may comprise an undiluted contrast agent.

According to a particular characteristic, in order to ensure the passage of the infusion liquid with the balloon inflated, a pressure differential is employed: The super-compliant balloon deploys from 5/6 bar for a maximum pressure of about 14/15 bar, while the second channel, or infusion conduit, supports up to about 35/40 bar. It therefore suffices to increase the pressure of the infusion liquid in order to provide the desired infusion rate. In practice, the catheter is connected to an automatic injection pump (not shown here) for programming the rate.

According to another particular embodiment, the device according to the invention is characterized in that it comprises at least one temperature sensor 32 positioned toward the distal end D of the catheter device, said temperature sensor 32 being positioned in order to measure a temperature of the infusion liquid LI outside said catheter device, in the vicinity of the aforementioned infusion orifices 16, 18, 20, 22.

According to another particular embodiment, the device according to the invention is characterized in that at least some infusion orifices 16, 18, 20, 22 are arranged, on said outer wall, at a distance from each other on the same axial plane of said catheter device, as is shown in FIG. 4.

According to another particular embodiment, the device according to the invention is characterized in that the infusion liquid is a heat transfer liquid introduced at a temperature below the temperature prevailing inside said conduit.

According to another particular embodiment, the device according to the invention is characterized in that, when the obstruction or occlusion can be dissolved in a suitable liquid, for example a kidney stone or gallstone, the infusion fluid is an infusion liquid comprising a product that dissolves the obstruction or occlusion. A person skilled in the art will know the dissolving products that can be used. A product that dissolves a calculus is, for example, ammonium chloride NH4Cl or ammonium nitrate NH4N00.

According to another particular embodiment, the device according to the invention is characterized in that the infusion liquid is a liquid comprising at least one medicament for treating the tissues near the obstruction or occlusion. A person skilled in the art will know the medicaments that can be used. As a medicament, it is possible, for example, to use a medicament chosen from the list given above.

According to a further particular embodiment, the device according to the invention is characterized in that the guidewire 30 comprises at least one or more temperature sensors 32, of which at least one sensor 32 is positioned on a distal part of the guide in order to measure the temperature of the infusion liquid infused after the aforementioned infusion orifices, at the distal side of the catheter device, downstream from the obstruction or occlusion in said conduit, as is shown in FIGS. 1 and 2.

According to another particular embodiment, the device according to the invention is characterized in that it comprises at least one visual marking system at a proximal position and/or at an intermediate position of the catheter device, and/or at a distal position, allowing the medical personnel to precisely locate the catheter device inside the conduit to be treated.

According to a further particular embodiment, the device according to the invention is characterized in that the visual marking system comprises one or more radiopaque markers provided at positions in order to precisely locate at least the position of the distal end of the catheter device, the infusion orifices and the obturating element.

According to a particular embodiment, the device according to the invention is characterized in that the aforementioned conduit 50 is a channel of the body of an animal or human being, chosen from the group consisting of a blood vessel, an artery, a coronary artery, the urinary tract, the esophagus and a pulmonary alveolus.

EXAMPLE 2 OF CATHETER ACCORDING TO THE INVENTION

A second embodiment is shown in FIGS. 5 to 10, in which the components having the same function bear the same reference numbers, but increased by 100.

Thus, the catheter has the general reference no. 110, the guidewire 130, the temperature sensor thereon 132, the sealing element 170, such as a balloon 172, supplied via a dedicated channel 180 defining a lumen 182 and opening into the interior 174 of balloon 172 through an opening 184.

In this second embodiment, the first element 128 is arranged with its axis parallel to the longitudinal axis X-X of the catheter device 110, in particular in such a way as to have a common wall 128a with the second tubular element 112, which here also defines the outer wall of the catheter device 110. In this case, according to one variant, the second channel 114 can be defined by the space present between the second tubular element 112 and the first tubular element 128.

According to an embodiment variant, the second channel 114 is closed at its distal end by a leaktight partition 114c in order to force the infusion liquid to pass through the infusion orifices 116, 118, 122.

Figure 9:
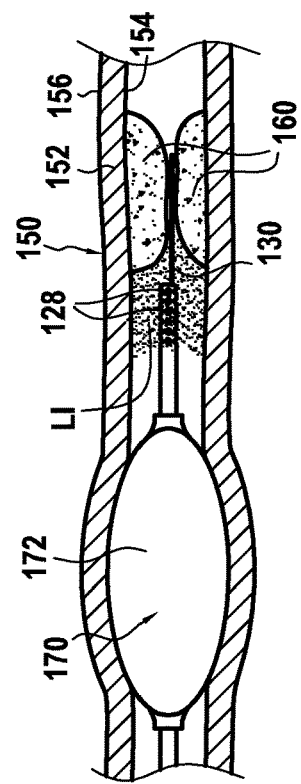
FIG. 9 shows an axial cross-sectional view along the section line IX-IX of FIG. 5.
Figure 10:
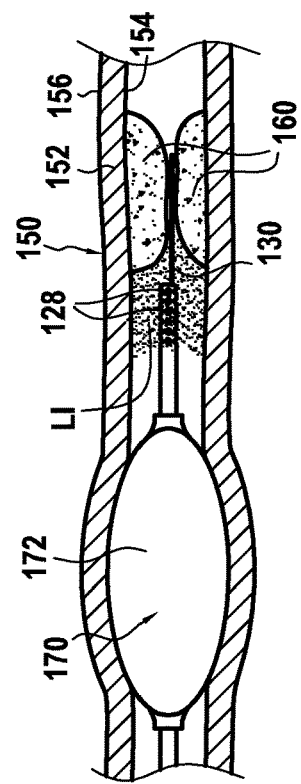
FIG. 10 shows the second embodiment of FIGS. 5 to 9, of the catheter device according to the present invention, in the working position, arranged upstream from an obstruction or occlusion to be treated, such as a calculus or concretion of the bladder, kidney or gallbladder.

According to another particular embodiment, the device according to the invention is characterized in that at least some infusion orifices, here 116, 118, 122, are arranged at a distance from each other on the same axis of said catheter device substantially parallel to the longitudinal axis of the device, as is shown in FIG. 9. This second embodiment of the infusion orifices is of course possible with the first embodiment of FIGS. 1 to 4, and vice versa.

EXAMPLE 3 OF CATHETER ACCORDING TO THE INVENTION

Figure 13:
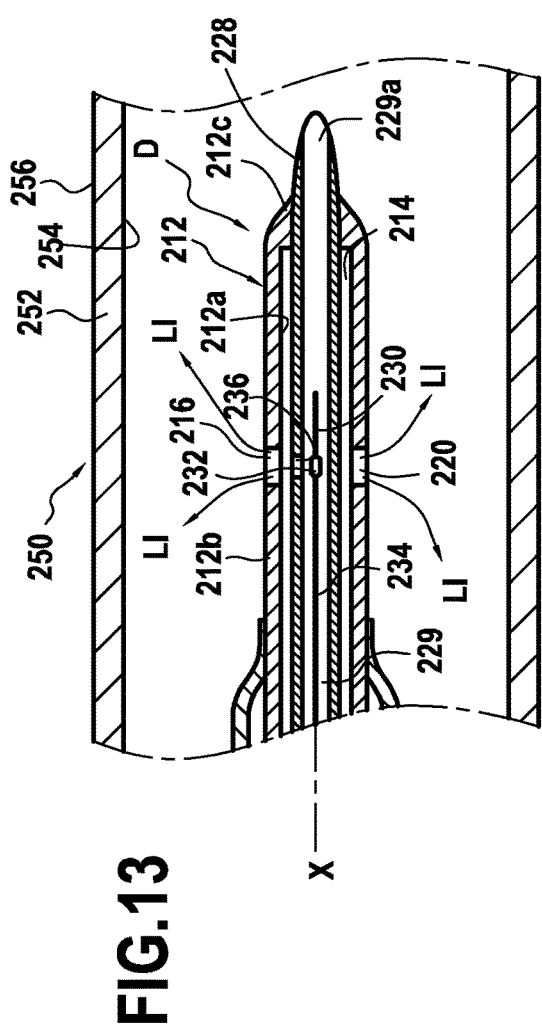
FIG. 13 shows an axial cross-sectional view along the same section line XII-XII of FIG. 11, but in the retracted position of the guidewire, with a temperature sensor device opposite an orifice communicating with the central channel passage of the guidewire.

A third embodiment is shown in FIGS. 11 to 13, in which the components having the same function bear the same reference numbers as in the previous two embodiments, but increased by 100.

Thus, the catheter here has the general reference no. 210, the guidewire 230, the temperature sensor thereon 232, the obturating element 270, such as a balloon 272, supplied via a dedicated channel 280 defining a lumen 282 and opening into the interior 274 of balloon 272 through an opening 284.

According to this third particular embodiment, the device according to the invention is characterized in that it comprises at least one inner orifice 236 passing through the wall of the inner tubular element 228 in order to establish a communication of the first channel 129 with the second channel 214 defined between the inner tubular element 228 and the outer tubular element 212, and in which the infusion liquid LI circulates, in the region of the outer orifices 216, 218, 220, 222 for infusion of the liquid to the outside of the catheter, in order to measure the temperature of the fluid in situ within the catheter, by virtue of the presence of the guidewire provided with a temperature sensor element 232, which is movable downstream from the outside until it lies opposite the inner orifice 236.

EXAMPLE 4 OF CATHETER ACCORDING TO THE INVENTION

Figure 14:
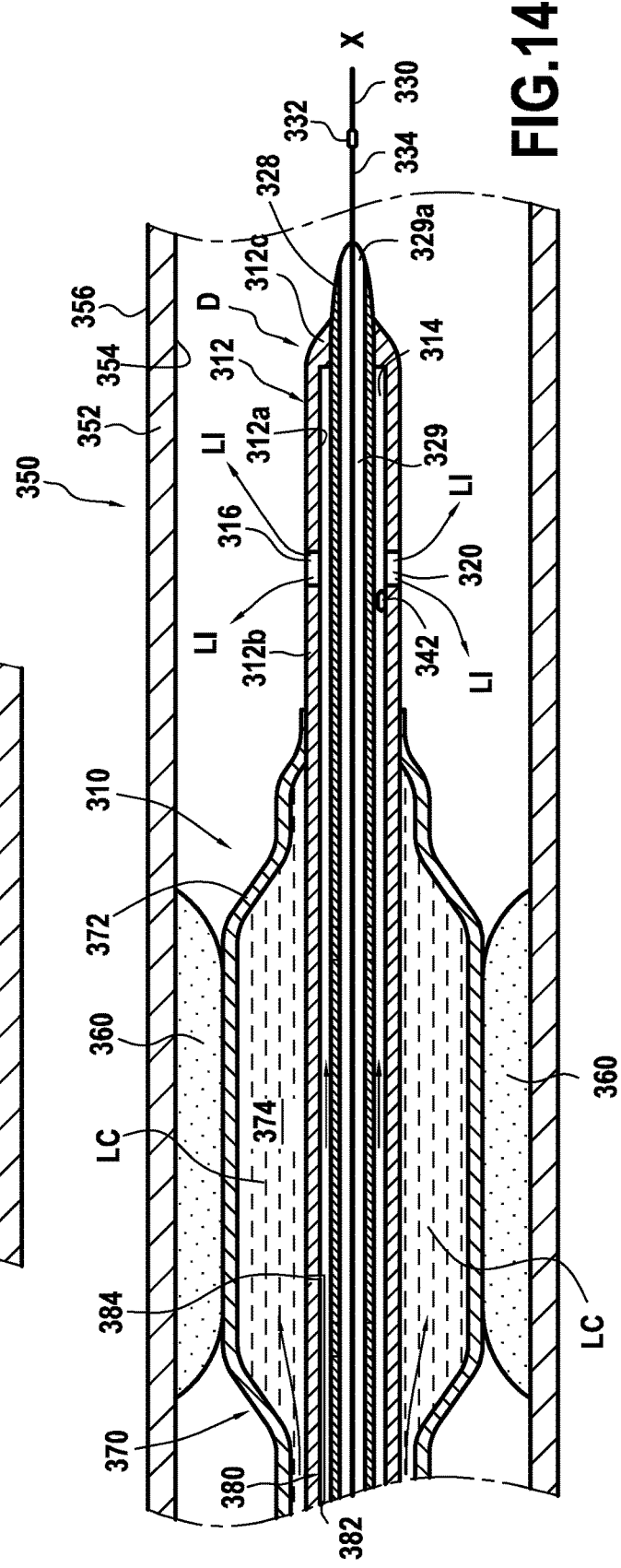
FIG. 14 shows an axial sectional view, similar to FIG. 2, of a fourth embodiment of a catheter device according to the present invention provided with a obturating element such as an inflation balloon positioned at and inside the obstruction to be treated and comprising a first temperature sensor on the guidewire; and a second temperature sensor positioned inside the channel passage of the infusion fluid and close to at least one infusion orifice, in order to measure the temperature of the infusion fluid in situ before it leaves through the infusion orifices, at the distal side of the catheter device.

A fourth embodiment is shown in FIG. 14, in which the parts having the same function bear the same reference numbers as in the previous three embodiments, but increased by 100.

Thus, the catheter here has the general reference no. 310, the guidewire 330 and the temperature sensor thereon 332, the sealing element 370, such as a balloon 372, supplied via a dedicated channel 380 defining a lumen 382 and opening into the interior 374 of balloon 372 through an opening 384.

According to this fourth particular embodiment, the device according to the invention is characterized in that it comprises at least one or more temperature sensors 332, 342, of which at least one temperature sensor 342 is positioned inside the catheter, here in the second channel 314 and close to at least one infusion orifice, here 320, in order to measure the temperature of the infusion fluid in situ before it leaves through the aforementioned infusion orifices, at the distal side of the catheter device.

According to this embodiment, the guidewire carrying the temperature sensor 332, arranged outside the catheter, can remain in a relatively fixed position without having to be retracted as in the third embodiment of FIGS. 11 to 13. Thus, the measurement of the temperature of the infusion liquid LI takes place simultaneously in situ inside the catheter prior to its infusion and outside after its infusion into the channel 350.

According to a second aspect, the invention relates to an infusion catheter device (10; 110) having a distal end (D) and a proximal end (P), configured to be introduced into a conduit (50; 150) having an inner wall (54; 154) and an outer wall (56; 156) and comprising at least one partial or total obstruction (60; 160) or occlusion to be treated, said device comprising at its distal end (D), on said outer surface, one or more infusion orifices (16; 116, 18; 118, 20, 22; 122) for an infusion liquid (LI), and, upstream from the one or more infusion orifices, at the proximal side (P) of the infusion catheter (10; 110), on said outer surface, at least one obturating element (70) for temporary obturating, configured to treat said obstruction (60) or occlusion and to perform the infusion of the infusion liquid (LI) downstream from the obturating element (70) and in the obturating position, to perform the treatment of at least one partial or total obstruction or occlusion present in a conduit which is advantageously a channel of the body of an animal or human being, chosen from the group consisting of a blood vessel, an artery, a coronary artery, the urinary tract, the esophagus and a pulmonary alveolus, and to simultaneously perform the infusion of the infusion liquid downstream from the obturating element in the obturating position thereof.

According to a third aspect, the invention also relates to a method for treating at least one partial or total obstruction or occlusion present in a conduit, said method being applicable to the four embodiments of the catheter device described above and comprising:

a) the introduction of a catheter device into said conduit, said catheter device being as defined according to any embodiment defined for the first aspect described above or below, in particular equipped with a temperature sensor at its distal end; this introduction being performed while the obturating device is in the rest position, until the obturating device is arranged near, particularly inside, the partial or total obstruction or occlusion, as shown in FIGS. 1 to 4 and 11 to 14, or upstream from the obstruction, as shown in the embodiment of FIGS. 5 to 10;

b) the guidewire is introduced through the catheter until its distal end is arranged downstream from the partial or total obstruction in said conduit.

According to a variant, and depending on the cases to be treated, the order of steps a) and b) can be reversed.

c) the placement of the obturating element in the temporary obturating position in order either to define a confined space arranged between the outer wall of the catheter device and the inner wall of the conduit to be treated, and the partial or total obstruction of said conduit (FIGS. 5 to 10), or to treat the obstruction or occlusion by compression (FIGS. 1 to 5 and 11 to 14);

d) the infusion of the infusion liquid, either in said confined space (FIGS. 5 to 10) or downstream from the obstruction or occlusion (FIGS. 1 to 5 and 11 to 14), through said infusion orifices, in order to ensure either the treatment of said partial or total obstruction present in said channel or the treatment of the conduit walls downstream from said obstruction or occlusion.

In a particular embodiment, this method entails the use of a heat-transfer infusion liquid regulated to a temperature for thermal treatment of the walls of the conduit downstream from the obstruction or occlusion.

In particular, when the aforementioned conduit is a channel of the body of an animal or human being, chosen from the group consisting of a blood vessel, an artery, a coronary artery, the urinary tract, the esophagus and a pulmonary alveolus, the temperature of the infusion liquid is regulated in order to obtain hypothermia of the tissues of said channel of the body.

According to a particular embodiment, following this thermal treatment, the method of the invention comprises a surgical treatment by inserting an expansion device such as a stent, well known to a person skilled in the art, into the region of the obstruction or occlusion.

According to a particular embodiment variant, this method also entails, after this expansion, a post-operative thermal treatment using the catheter device according to the invention in the region of the partial or total obstruction in said conduit, in order to improve the recovery of the tissues of the body channel.

EXAMPLE 5—USE OF THE EMBODIMENT OF FIGS. 1 TO 4 AND 11 TO 14 IN CARDIAC SURGERY OR INTERVENTIONAL CARDIOLOGY

In the context of cardiac surgery, the aim of the invention is to provide selective hypothermia, i.e. selective cooling of the portion of the heart muscle at risk in patients with acute myocardial infarction. This cooling (hypothermia) must begin a few minutes (about 10 minutes) before the occluded artery, i.e. the artery responsible for the infarction, is recanalized (reopened). This cooling must continue for a few minutes (10 minutes) even after the recanalization of the artery. These times are only indicative and may vary between patients and according to the results obtained in early studies.

It is known that a myocardial infarction is caused by occlusion of a coronary artery. This sudden occlusion threatens the survival of the part of the heart muscle that depends on this artery. Rapid recanalization of this blocked artery is able to limit the extent of the damage. This rapid recanalization is part of the treatment of the acute phase of the infarction and is called primary angioplasty. However, it has been shown that abrupt reperfusion of the artery is itself responsible for an extension of the necrosis of the cardiac cells. The latter is called "reperfusion damage". Some of the benefit of primary angioplasty is thus wiped out by the problems associated with reperfusion. It is precisely this reperfusion damage that is avoided by the hypothermia method according to the invention. The ultimate extent of the infarct may thus be limited by this method of hypothermia. The extent of the infarct is by far the most important prognostic factor after a myocardial infarction. Therefore, the hypothermia according to the invention makes it possible to limit the extent of the infarct and thus improve the prognosis of the patients.

The advantage of the method of selective hypothermia according to the invention is that the desired temperature is reached very quickly, only the part of the heart muscle at risk is cooled, and the volume overload is greatly reduced. Therefore, few if any systemic effects are to be feared.

As will be clear from the foregoing description, the catheter according to the invention combines the features of a conventional balloon catheter and of an infusion catheter and has dimensions very similar to those of a conventional balloon catheter. It can therefore be constructed as follows.

The catheter generally has three channels or lumens:
- a first channel or lumen 29; 229, or 329, coaxial, shown in FIGS. 1 to 4 and 11 to 14, i.e. a first lateral channel 128, called monorail, defining a first lateral lumen, shown in FIGS. 5 to 10, which allows the catheter to be advanced on any guidewire 30, 130, 230, 330 of 0.014 inches, and therefore also on a guidewire 30, 130, 230, 330 provided with a temperature and/or pressure sensor 32, 132, 232, 332, or vice versa;
- a second channel or lumen 14, 114, 214, 314, generally formed by the outer wall of the second tubular element 12, 112, 212, 312 of the catheter 10, 110, 210, 310, which communicates from the proximal part as far as the distal infusion orifices 16, 18, 20, 22; or 116, 118, 122; or 216, 218, 220, 222; or 316, 318, 320, 322, here lateral, which are situated at the distal part and through which the infusion liquid, which may be a physiological liquid or other liquid, is infused from the infusion channel LC proximally;
- a third channel 80, 180, 280, 380 defining a third lumen 82, 182, 282, 382, communicating via an opening 84, 184, 284, 384 with the interior of the obturating element, here a balloon 72, 172, 272, 372, which can be deflated to a rest position or inflated from this rest position to an inflated working position shown in FIGS. 1 to 3, 6, 8, 10, 11, 13 and 14. This balloon inflation can be performed from the channel LC proximally by insufflation of a gas or a liquid which, if so desired, can comprise a diluted contrast medium by which it is possible to check the exact position of the catheter, and in particular of the balloon, relative to the obstruction or occlusion, and of the infusion orifices.

The inflation and deflation of the balloon, for example situated between one and several centimeters or several millimeters upstream from the distal lateral infusion orifices, is carried out in the same way as for conventional balloons. However, according to a particular feature, in order to ensure the passage of the infusion liquid with the balloon inflated, a pressure differential is employed: The super-compliant balloon deploys from 5/6 bar for a maximum pressure of about 14/15 bar, whilst the second channel, or infusion conduit, supports up to about 35/40 bars. It therefore suffices to increase the pressure of the infusion liquid in order to ensure the desired infusion rate while the balloon is inflated. In practice, the catheter is connected to an automatic injection pump (not shown here) for programming the rate.

In an embodiment of cardiac surgery with entry near the heart, the catheter can have a length of about 20 to 22 cm, and it can have an external diameter of less than one mm, for example 0.95 mm. The infusion orifices can, for example, have a diameter of about 150 micrometers and can be situated at 7 to 8 mm from the distal end of the catheter and be positioned at 0°, 180° and/or 90° and 270°, hence diametrically opposite and/or offset axially along the catheter axis, as is shown in the four embodiments of FIGS. 1 to 14.

It is noted that the proximal end of the catheter is thus provided with two connectors. The first is for connecting an infusion pump for infusion liquid LI, and the second C2 is for connecting a syringe or a pump for inflating or deflating the balloon 72, 172, 272, 372.

Selective Cooling Procedure:

The patient who presents with an acute myocardial infarction, and who would benefit from primary angioplasty, is placed on the catheterization table exactly as usual. The delivery catheter 10, 110, 210, 310 is advanced through the femoral artery or radial artery.

The guidewire 30, 130, 230, 330, provided with a thermistor, for example the PressureWire from St Jude Medical, is advanced through the delivery catheter. This guidewire is advanced into the distal part of the artery, through the occlusion responsible for the infarct.

The catheter 10, 110, 210, 310 is connected to the infusion pump, and the tubing is rinsed of any air bubbles. The catheter is then mounted on the guidewire 30, 130, 230, 330, and the balloon 72, 172, 272, 372 is advanced to the coronary occlusion 60, 160, 260 or 360. The balloon 72, 172, 272, 372 is immediately inflated at this region in order to avoid reperfusion of the infarcted segment.

The infusion of infusion liquid LI, for example sterilized physiological liquid which may be heparinized at the desired thermal treatment temperature, starting for example at the temperature of the operating room, is then started. This infusion during the occlusion by the balloon is maintained for 10 minutes.

The distal temperature is monitored by means of at least one temperature sensor or thermistor 32, 132, 232, 332, 342 located in the distal part of the artery.

In the initial study protocol, the temperature in the distal part of the coronary artery must be about 6 to 8 degrees lower than the blood temperature. Under these conditions, a temperature about 4 degrees lower than that of blood was obtained in the nearby myocardial tissue.

After about 10 minutes, the infusion liquid, for example physiological saline, at room temperature is replaced by infusion liquid, for example physiological saline, at a temperature of about 4 degrees Celsius, and the occlusion balloon is simultaneously deflated. This allows the blood to flow along the catheter and mix with the cold physiological saline. Again, the temperature of the mixture is controlled by the thermistor located in the distal portion of the artery. This temperature must be 4 to 5 degrees below the temperature of the blood. It is known that under these conditions the temperature of the adjacent myocardium is about 4 degrees below the temperature of the blood.

After about 10 minutes, the infusion of physiological saline is interrupted.

Finally, the catheter 10, 110, 210, 310 according to the invention is removed, and a stent is placed with another suitable catheter according to the local routine.

Of course, the duration of infusion and the temperature of the infused liquid are variable. Consequently, the method according to the invention also applies to other durations of infusion and other temperatures.

As regards the distal infusion orifices, the catheter is described with either four lateral orifices in FIGS. 1 to 4 and 11 to 14, or with three lateral orifices in FIGS. 5 to 10 in the same axial plane, and one distal orifice, but other combinations are of course conceivable, also with a distribution of the orifices along an axis parallel to the longitudinal axis of the device, as is shown in FIGS. 5 to 10.

The catheter according to the invention can be used with other guidewires, and the insertion procedure can be reversed.

The catheter according to the invention is therefore a combination of an infusion catheter and of a balloon catheter. The purpose of this combination is to permit simultaneously the occlusion of the vessel and the infusion of an infusion liquid in order to provide treatment of tissues arranged after the occlusion according to the embodiment of FIGS. 1 to 4 and 11 to 14, or dissolution of the occlusion according to the embodiment of FIGS. 5 to 10, as is shown below.

EXAMPLE 6: USE OF THE EMBODIMENT OF FIGS. 5 TO 10 FOR DESTROYING OBSTRUCTIONS SUCH AS CALCULI OR CONCRETIONS

Using a procedure similar to the one described for Example 5, but placing the infusion orifices before the obstruction or occlusion such as a calculus or concretion in the urinary tract, it is possible, after inflation of the balloon 172, to infuse a liquid for destroying or dissolving the occlusion over the required period of time and with normal monitoring.

Likewise, according to another variant which is applicable particularly to destroying an obstruction or occlusion such as a calculus or concretion, the second channel 114 can be open at its distal end in order to allow the infusion liquid to pass not only through the infusion orifices 116, 118, 122 but also through the distal opening of the second channel. This variant is applicable to the four embodiments of FIGS. 1 to 14.

The catheter device according to the invention is therefore very versatile and can be used to treat various types of obstructions or occlusions in different types of conduits, as has been described above.

The invention thus covers all the technical equivalents of the means described and shown in FIGS. 1 to 14. FIGS. 1 to 14 moreover form an integral part of the invention and complement the description of the invention.

The invention claimed is:

1. A one piece infusion catheter device having an elongate, substantially tubular shape defining a longitudinal axis X-X, an outer wall and an inner wall and defining a distal end and a proximal end, configured to be introduced into a conduit having an inner wall and an outer wall and having at least one partial or total obstruction or occlusion to be treated, said one piece infusion catheter device comprising, at a distal end, on said outer wall, one or more infusion orifices for an infusion liquid, and, upstream from the one or more infusion orifices, on said catheter outer wall, at least one temporary obturating element having a rest non obturating position and a working obturating position for temporary obturating said conduit, wherein when the one piece infusion catheter device is introduced into the conduit, said at least one temporary obturating element is spaced apart from the one or more infusion orifices a distance sufficient to have said at least one temporary obturating element located upstream, or inside, said obstruction or occlusion in the conduit and said one piece infusion catheter device performing the infusion of the infusion liquid only downstream from the at least one temporary obturating element while in the working obturating position, and at least downstream from the obstruction or occlusion.

2. The one piece infusion catheter device as claimed in claim 1, wherein the at least one temporary obturating element comprises an inflatable balloon having a rest position in the deflated state and a working position in the inflated state, arranged outside the one piece infusion catheter device and supplied with an inflation fluid through an inflation channel arranged inside or at the surface of the catheter and wherein the balloon inflation fluid can comprise a diluted or undiluted contrast agent.

3. The one piece infusion catheter device as claimed in claim 1, wherein at least some infusion orifices are arranged on the outer wall of the one piece infusion catheter device at a distance from each other on the same axial plane of said one piece infusion catheter device.

4. The one piece infusion catheter device as claimed in claim 1, wherein at least some infusion orifices are arranged on the outer wall of the one piece infusion catheter device at a distance from each other on the same axis of said one piece infusion catheter device substantially parallel to the longitudinal axis of the one piece infusion catheter device.

5. The one piece infusion catheter device as claimed in claim 1, comprising a proximal channel for infusion of the infusion liquid, which is a heat-transfer liquid introduced at a temperature below the temperature prevailing inside said conduit.

6. The one piece infusion catheter device as claimed in claim 1 comprising a proximal channel for infusion of the infusion liquid.

7. The one piece infusion catheter device as claimed in claim 1 wherein the infusion liquid comprises at least one medicament for treating the tissues near the obstruction or occlusion.

8. The one piece infusion catheter device as claimed in claim 1, wherein the catheter comprises a guidewire channel for insertion of a guidewire and the guidewire comprises at least one or more temperature sensors, of which at least one of the temperature sensors is positioned on a distal part of the guidewire to measure the temperature of the infusion fluid, downstream from the one or more infusion orifices and at least downstream of the obstruction or occlusion, at the distal side of the one piece infusion catheter device.

9. The one piece infusion catheter device as claimed in claim 1, comprising at least one or more temperature sensors, of which at least one sensor is positioned inside the catheter and close to at least one infusion orifice, in order to measure the temperature of the infusion fluid in situ before it leaves the one piece infusion catheter device through the one or more infusion orifices, at the distal side of the one piece infusion catheter device.

10. The one piece infusion catheter device as claimed in claim 1, wherein the one piece infusion catheter device is shaped to be introduced into the conduit which is a channel of the body of an animal or human being, selected from the group consisting of a blood vessel, an artery, a coronary artery, the urinary tract, the esophagus and a pulmonary alveolus.

11. A one piece infusion catheter device having an elongate, substantially tubular shape defining a longitudinal axis X-X, an outer wall and an inner wall and defining a distal end and a proximal end, configured to be introduced into a conduit having an inner wall and an outer wall and having at least one partial or total obstruction or occlusion to be treated, said one piece infusion catheter device comprising, at a distal end, on said outer wall, one or more infusion orifices for an infusion liquid, and, upstream from the one or more infusion orifices, on said catheter outer wall, at least one temporary obturating element having a rest non obturating position and a working obturating position for temporary obturating said conduit, wherein said one piece infusion catheter device comprises:
    a. a first element, which is substantially tubular and made of a flexible but substantially non-expandable and substantially non-collapsible material, configured to define a first channel for receiving a guidewire, and having an outlet opening at the distal end of the one piece infusion catheter device;
    b. a second element, which is substantially tubular and made of a flexible but substantially non-expandable and substantially non-collapsible material, configured to define a second channel for receiving the infusion liquid, said one or more infusion orifices passing through the wall of the second element in order to infuse the infusion liquid from the second channel to the outside of the one piece infusion catheter device; and
    c. wherein said catheter comprises at least one or more temperature sensors, of which at least one of the temperature sensors is configured to be positioned on a distal part of the guidewire to measure the temperature of the infusion fluid, downstream from the one or more infusion orifices and at least downstream of the obstruction or occlusion.

12. The one piece infusion catheter device as claimed in claim 11, wherein the first element is arranged coaxially with respect to the one piece infusion catheter device whilst the second element is likewise coaxial while having a larger diameter than the first element, thus being concentric and having its wall which defines the outer wall of the one piece infusion catheter device, said outer wall comprising the one or more infusion orifices.

13. The one piece infusion catheter device as claimed in claim 11, wherein the first element is arranged with its axis parallel to the longitudinal axis of the one piece infusion catheter device to have a common wall with the second element of the one piece infusion catheter device, whilst the second element is defined by the outer wall of the one piece infusion catheter device, thereby defining the second channel between the second element and the first element.

14. The one piece infusion catheter device as claimed in claim 11, wherein, when the obstruction or occlusion can be dissolved in a suitable liquid, said one piece infusion catheter device comprises a proximal channel for infusion of the infusion liquid, which is an infusion liquid comprising a product that dissolves the obstruction or occlusion.

15. The one piece infusion catheter device of claim 14, wherein the obstruction or occlusion, which can be dissolved in a suitable liquid, is selected from a kidney stone and a gallstone.

16. The one piece infusion catheter device as claimed in claim 11, comprising at least one inner orifice communicating with the second channel defined between the inner tubular element and the outer tubular element and in which circulates the infusion liquid, said at least one inner orifice being located in the vicinity of at least one of the outer orifices for infusion of the infusion liquid to the outside of the catheter, to measure the temperature of the infusion liquid, by the presence of the guidewire provided with a temperature sensor element movable downstream from the outside of the catheter until said guidewire lies opposite the inner orifice.

17. A method for treating at least one partial or total obstruction or occlusion present in a conduit, comprising:
    a) the introduction of a catheter device into said conduit, said catheter device being as defined according to claim 1, equipped with a temperature sensor at its distal end; this introduction being performed while the at least one temporary obturating element is in the rest non obturating position, until the at least one obturating element is arranged near, particularly inside, the partial or total obstruction or occlusion, or upstream from the obstruction or occlusion, and the one or more infusion orifices are located downstream of the obstruction or occlusion;
    b) a guidewire is introduced through the catheter device until its distal end is arranged downstream from the partial or total obstruction or occlusion in said conduit; or, alternatively, the order of steps a) and b) can be reversed;
    c) the placement of the at least one temporary obturating element in the working obturating position in order either to define a confined space arranged between the outer wall of the catheter device and the inner wall of the conduit to be treated, and the partial or total obstruction or occlusion of said conduit, or to treat the obstruction or occlusion by compression;
    d) the infusion of the infusion liquid downstream from the obstruction or occlusion, through said one or more infusion orifices, to ensure the treatment of the conduit walls downstream from said obstruction or occlusion.

18. The method as claimed in claim 17, comprising using a heat-transfer infusion liquid regulated to a temperature performing thermal treatment of the walls of the conduit downstream from the obstruction or occlusion.

19. The method as claimed in claim 18, wherein, following this thermal treatment, performing a surgical treatment by inserting an expansion device in the region of the obstruction or occlusion.

20. The method as claimed in claim 19, wherein the expansion device comprises a stent.

21. The method as claimed in claim 19, wherein, after this expansion is performed, a post-operative thermal treatment is carried out using the catheter device in the region of the partial or total obstruction or occlusion in said conduit, in order to improve the recovery of the tissues of the body channel.

22. The method as claimed in claim 17, wherein the conduit is a channel of the body of an animal or human being, selected from the group consisting of a blood vessel, an artery, a coronary artery, the urinary tract, the esophagus and a pulmonary alveolus.

23. The method as claimed in claim 22, wherein the temperature of the infusion liquid is regulated in order to obtain hypothermia of the tissues of said channel of the body.

24. A one piece infusion catheter device having an elongate, substantially tubular shape defining a longitudinal axis X-X, an outer wall and an inner wall and defining a distal end and a proximal end, configured to be introduced into a conduit having an inner wall and an outer wall and having at least one partial or total obstruction or occlusion to be treated, said one piece infusion catheter device comprising:
  a. a first element, which is substantially tubular and made of a flexible but substantially non-expandable and substantially non-collapsible material, configured to define a first channel for receiving a guidewire, and having an outlet opening at the distal end of the one piece infusion catheter device;
  b. a second element, which is substantially tubular and made of a flexible but substantially non-expandable and substantially non-collapsible material, configured to define a second channel for receiving an infusion liquid, and one or more infusion orifices passing through the outer wall of the second element in order to infuse the infusion liquid from the second channel to an outside of the one piece infusion catheter device;
  wherein the first element is arranged with an axis parallel to the longitudinal axis X-X of the one piece infusion catheter device to have a common wall with the second element of the one piece infusion catheter device, whilst the second element is defined by the outer wall of the one piece infusion catheter device, thereby defining the second channel between the second element and the first element,
  wherein said one piece infusion catheter device further comprises, at a distal end, on said outer wall, the one or more infusion orifices for the infusion liquid, and, upstream from the one or more infusion orifices, on said catheter outer wall, at least one temporary obturating element having a rest non obturating position and a working obturating position for temporary obturating said conduit, wherein when the one piece infusion catheter device is introduced into the conduit, said at least one temporary obturating element is spaced apart from the one or more infusion orifices a distance sufficient to be located upstream of, or inside, said obstruction or occlusion in the conduit and the one piece infusion catheter device is configured to perform the infusion of the infusion liquid in a direction substantially perpendicular to said longitudinal axis and only downstream from the at least one temporary obturating element and in the working obturating position and at least downstream from the obstruction or occlusion.

25. The one piece infusion catheter device as claimed in claim 24, wherein the guidewire comprises at least one or more temperature sensors, of which at least one temperature sensor is positioned on a distal part of the guidewire to measure the temperature of the infusion fluid, downstream from the one or more infusion orifices and downstream from the obstruction or occlusion, at the distal side of the one piece infusion catheter device.

26. The one piece infusion catheter device as claimed in claim 24, wherein the at least one temporary obturating element comprises an inflatable balloon having a rest position in the deflated state and a working position in the inflated state, arranged outside the one piece infusion catheter device and supplied with an inflation fluid through an inflation channel arranged inside or at the surface of the catheter and wherein the balloon inflation fluid can comprise a diluted or undiluted contrast agent.

27. The one piece infusion catheter device as claimed in claim 24, wherein at least some infusion orifices are arranged on the outer wall of the one piece infusion catheter device at a distance from each other on the same axial plane of said one piece infusion catheter device.

28. The one piece infusion catheter device as claimed in claim 24, wherein at least some infusion orifices are arranged on the outer wall of the one piece infusion catheter device at a distance from each other on the same axis of said one piece infusion catheter device substantially parallel to the longitudinal axis of the one piece infusion catheter device.

29. The one piece infusion catheter device as claimed in claim 24, comprising at least one inner orifice providing communication between the first channel and the second channel in which circulates the infusion liquid, said at least one inner orifice being located in the vicinity of at least one of the infusion orifices for infusion of the infusion liquid to the outside of the catheter, to measure the temperature of the infusion liquid, by the presence of the guidewire provided with a temperature sensor element movable downstream from the outside of the catheter until said guidewire lies opposite the inner orifice.

30. The one piece infusion catheter device as claimed in claim 24, comprising at least one or more temperature sensors, of which at least one temperature sensor is positioned inside the catheter and close to at least one infusion orifice, in order to measure the temperature of the infusion fluid in situ before it leaves the one piece infusion catheter device through the one or more infusion orifices, at the distal side of the one piece infusion catheter device.

31. The one piece infusion catheter device as claimed in claim 24, comprising a proximal channel for infusion of the infusion liquid, which is a heat-transfer liquid introduced at a temperature below the temperature prevailing inside said conduit.

32. The one piece infusion catheter device as claimed in claim 24, wherein the infusion liquid comprises at least one medicament for treating the tissues near the obstruction or occlusion.

33. The one piece infusion catheter device as claimed in claim 24, wherein the one piece infusion catheter device is shaped to be introduced into the conduit which is a channel of the body of an animal or human being, selected from the group consisting of a blood vessel, an artery, a coronary artery, the urinary tract, the esophagus and a pulmonary alveolus.

* * * * *